United States Patent [19]

Dixon, Jr.

[11] Patent Number: 4,649,483

[45] Date of Patent: Mar. 10, 1987

[54] METHOD FOR DETERMINING FLUID SATURATION IN A POROUS MEDIA THROUGH THE USE OF CT SCANNING

[75] Inventor: James R. Dixon, Jr., Dallas, Tex.

[73] Assignee: Mobil Oil Corporation, New York, N.Y.

[21] Appl. No.: 656,553

[22] Filed: Oct. 1, 1984

[51] Int. Cl.$^4$ ...................... G01N 23/04; G03B 41/16
[52] U.S. Cl. ...................................... 364/422; 250/256
[58] Field of Search ................... 364/422, 420; 378/5; 324/366, 367; 73/38; 250/255, 256

[56] References Cited

U.S. PATENT DOCUMENTS

| | | | |
|---|---|---|---|
| 4,157,472 | 6/1979 | Beck, Jr. et al. | 250/445 T |
| 4,283,629 | 8/1981 | Habermehl et al. | 250/445 T |
| 4,359,687 | 11/1982 | Vinegar | 324/366 |
| 4,399,509 | 8/1983 | Hounsfield | 364/414 |
| 4,422,177 | 12/1983 | Mastronardi et al. | 378/17 |
| 4,571,491 | 2/1986 | Vinegar | 378/207 |

OTHER PUBLICATIONS

"Computed Tomographic Analysis of Meteorite Inclusions", *Science*, vol. 219, Jan. 28, 1983, pp. 383–384.

*Primary Examiner*—Jerry Smith
*Assistant Examiner*—G. Hayes
*Attorney, Agent, or Firm*—Alexander J. McKillop; Michael G. Gilman; George W. Hager, Jr.

[57] ABSTRACT

Multi-phase fluid saturation in a sample of a porous media is determined through computed tomographic scanning. The sample is scanned with X-rays of differing energies in both the fluid saturated and fluid-extracted states. Each of the extracted fluids is also scanned at differing X-ray energies. The computed tomographic images produced are utilized in the determination of the X-ray mass attenuation coefficients for the sample and the extracted fluids. From these mass attenuation coefficients, the weight fractions and volume fractions of each of the extracted fluids are determined.

9 Claims, 1 Drawing Figure

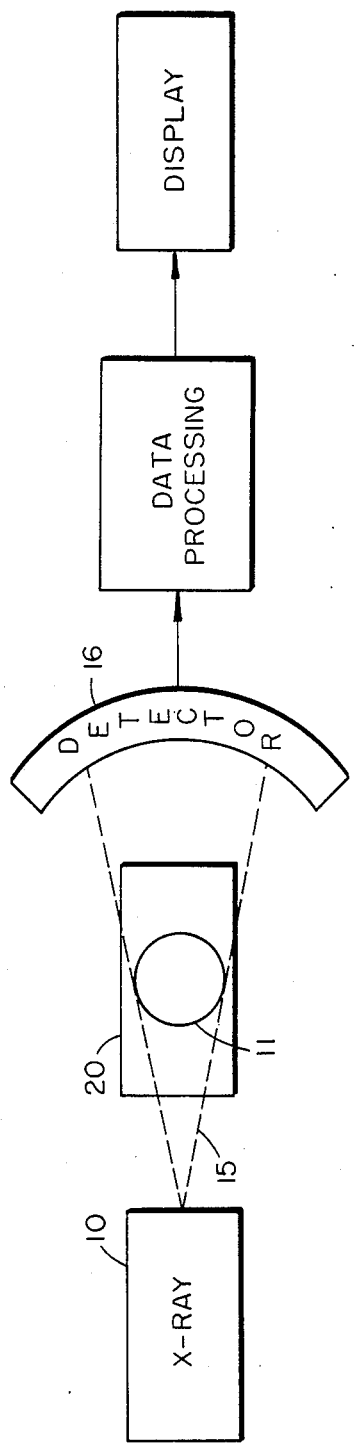

METHOD FOR DETERMINING FLUID SATURATION IN A POROUS MEDIA THROUGH THE USE OF CT SCANNING

BACKGROUND OF THE INVENTION

Computed tomography (CT) technology has been in use in the medical field for several years. Such CT scanning instruments produce a cross-sectional view through the subject material along any chosen axis. A two-dimensional X-ray image of electron density variations within the object scanned is produced. The advantages of CT scanning over conventional radiography is found in its much clearer images and its superior density resolution. In medical CT scanners, an X-ray source and a detector array circle a patient in a period of about 2 to 9 seconds and produces an image with maximum resolutions of 0.25 mm in the X-Y plane. This plane can be moved in discrete intervals to obtain information in 3 dimensions. For more details of such medical CT scanners, reference may be made to U.S. Pat. No. 4,157,472 to Beck, Jr. and Barrett (Assignee General Electric Company) and U.S. Pat. No. 4,399,509 to Hounsfield (Assignee EMI Limited).

Many other applications of CT scanning can also be made. For example, in an article entitled, "Computed Tomographic Analysis of Meteorite Inclusions", *Science*, pages 383-384, Jan. 28, 1983, there is described the non-destructing testing of meteorites for isotopic anomalies in calcium- and aluminum-rich inclusions of heterogeneous materials, such as Allende. The CT scanning equipment described in such article is the Deltascan 2020 from Technicare. In a further application, CT scanning has been applied to the non-destructive testing of wood materials, such as for disease in living trees, see U.S. Pat. No. 4,283,629 to Habermehl. In a yet further application, CT scanning has been applied to the examination of non-living objects, such as motors, ingots, pipes, etc., see U.S. Pat. No. 4,422,177 to Mastronardi, et al. (Assignee American Science and Engineering, Inc.).

More recently, the CT scanning technology has been applied to the field of energy research for examining the interior of stationary or slowly changing earth materials, such as coal, shale and drilling cores. Processes involved in coal gasification and combustion have been monitored using time-lapse CT imagery to observe changes in density (e.g., thermal expansion, fracturing, emission of gases, consumption by combustion) during progressive heating in a controlled atmosphere. Core flooding experiments can now be carried out with CT scanning to aid in enhanced oil recovery and fluid mobility control. For example, the permeability of materials within core samples to various fluids at varying conditions of temperature and pressure can be determined. Such experiments might involve flushing a fluid through a core sample and monitoring the shape of the fluid fronts. By subtracting the images of the cores before and after flooding, the exact shapes of the fluid front was determined. Such core flood experiments allows the interior of the core sample to be observed without disturbing the sample. The sweep efficiency and flow paths of fluids of interest may now be studied on the scale of millimeters. The penetration of X-rays allows experiments to be performed with up to 4 inch diameter core samples.

Drilling fluids can be analyzed by CT scanning as such fluids are characterized by high density brines, various organics and several compositionally different weighting agents. Formation damage can be investigated since CT scanning can detect migration of clays, absorption of organics and the reversibility of completion fluid penetration. Shale oil recovery can be aided as CT scanning could detect penetration by solvents and could directly measure structure changes on retorting. Rock fractures can be identified.

SUMMARY OF THE INVENTION

In accorance with the present invention, there is provided a method for determining the multi-phase fluid saturation in a porous media. A sample of the porous media is scanned with X-rays of differing energies and computed tomographic images are produced. The multi-phase fluid is extracted from the sample. The fluid extracted sample is scanned with X-rays of the differing energies and computed tomographic images are produced. The extracted fluids are scanned with the X-rays of differing energies and computed tomographic images are produced. From these images, the X-ray mass attenuation coefficients for the sample and each phase of the extracted fluid are determined for the differing energies of X-rays. From the X-ray mass attenuation coefficients, the weight fractions and volume fractions of each phase of the extracted fluid are determined.

In a further aspect, the fluid-extracted sample of porous media is air filled prior to being X-ray scanned. During excessive scanning times, the sample will be cooled, such scanning times being in the order of up to one minute or longer.

BRIEF DESCRIPTION OF THE DRAWING

The sole FIGURE illustrates a computed tomography system for use in the method of the present invention.

DESCRIPTION OF THE PREFERRED EMBODIMENT

The method of the present invention applies conventional CT scanning to the determination of fluid saturation in porous media. More particularly, the present invention is applied to the determination of the oil, gas and brine content of core samples taken from subsurface formations of interest.

Computed tomography (CT) produces a display or image of the density distribution in a cross-section or transverse slice of a material sample, such as a core sample from a subsurface formation. Such CT image can be produced for a core sample by use of the CT scanning system illustrated in the FIGURE. X-ray energy provided by the X-ray tube 10 passes through the core sample 11 and falls on the detector array 16. Rotation and indexing of core sample 11 within the X-ray fan beam 15 is provided by the gantry 20. After a desired number of scans are completed for a sample slice, the sample is indexed one slice width through the X-ray fan beam to place the next adjacent sample slice within the path of the X-ray fan beam. In this manner, a 3-D tomographic presentation can be made of the entire sample by compositing the cross-sectional views of each of the scan slices. Such a CT scanning system, while not forming a part of the present invention, is used in accordance with the method of the present invention to determine the presence of several different fluid phases within the pore spaces of a core sample simultaneously. For a more detailed description of a CT scanning system which may be utilized in the method of the present invention, reference may be made to each of the aforementioned U.S. patents and the referenced *SCIENCE* article, the teachings of which are incorporated herein by reference.

In accordance with the present invention, a porous sample material with a plurality of fluid phases to be identified is positioned by the gantry 20 within the fan beam path 15 of X-ray energy. X-ray scans may be performed on any area of the material by indexing the gantry. Each scan is performed by rotating the sample 360° within the fan beam path 15 for a given index position. Scanning times up to one minute, or longer, may be employed as radiation limitations on the sample are not the same concern as in medical scanning. However, for such greater scan times, and especially if a plurality of scans are to be recorded for each sample slice, suitable cooling of the sample will be required, such as the mounting of the sample within a water bath. Two distinct X-ray scans are carried out for each desired index position, each scan being at a different X-ray energy level. Such energy levels may be 100 and 150 kilovolts, for example. After completion of the CT scanning, the sample material is flushed firstly with solvents and secondly with air to remove all the fluid phases. The extracted fluid, or samples thereof, is placed in a suitable container and saved. The air-filled sample material is then scanned with the same two X-ray energies. A difference is determined between the CT images recorded for this air-filled sample at two different energies and the CT images recorded for the fluid-saturated sample at the respective energies. The resulting CT images, one for each energy, provide fluid saturation information exclusive of porous media effects. Such images are, in effect, two-dimensional maps of "CT number". The computer tomographic number ($N_{CT}$) is a numerical measure of the X-ray absorption properties of the sample of material being scanned by the X-ray fan beam and is routinely provided by the CT scanning system, as is more fully described in the aforementioned U.S. Pat. Nos. 4,283,629 and 4,399,509. Such a CT number is defined as:

$$N_{CT} = (\mu_M - \mu_W)/\mu_W \times 1000 \quad (1)$$

where
$\mu$ = X-ray mass attenuation coefficient,
M = material (or fluid) scanned, and
W = water.

For each X-ray energy there is a specific $\mu_M$ and $\mu_W$. From these measured CT numbers and previously measured values for $\mu_{W(1)}$ and $\mu_{W(2)}$, the X-ray mass attenuation coefficients at each energy, $\mu_{M(1)}$ and $\mu_{M(2)}$ for the material scanned is determined from equation (1).

Next, the extracted fluid, or samples thereof, is scanned at the same two X-ray energies. Alternatively, the extracted fluid may be separated into each of its fluid phases and each phase scanned independently. The average intensity of the images resulting from these scans establish the CT numbers for the fluids. From these CT numbers, the X-ray mass attenuation coefficients ($\mu_{a(1)}, \mu_{a(2)}, \mu_{b(1)}, \mu_{b(2)}, \mu_{c(1)}$ and $\mu_{c(2)}$) are obtained where a, b and c represent the three fluids and (1) and (2) represent the two scan energies.

The mass attenuation coefficient for a mixture is:

$$\mu_M = \sum_i X_i \mu_i, \quad (2)$$

where $X_i$ is the weight fraction of material i. Therefore, for the three fluid phases in the material sample, the mass attenuation coefficient for each energy is:

$$\mu_{M(1)} = X_a \mu_{a(1)} + X_b \mu_{b(1)} + X_c \mu_{c(1)} \quad (3)$$

$$\mu_{M(2)} = X_a \mu_{a(2)} + X_b \mu_{b(2)} + X_c \mu_{c(2)} \quad (4)$$

These two equations can then be combined with:

$$1 = X_a + X_b + X_c, \quad (5)$$

to create a series of three equations with three unknowns $X_a$, $X_b$ and $X_c$ for the weight fractions of the three fluid phases.

After determining the weight fractions of the three fluid phases, the volume fractions are determined by multiplying the weight fraction for each fluid phase by the density of that phase.

While preferred embodiments of the method of the present invention have been described and illustrated, numerous modifications or alterations may be made without departing from the spirit and scope of the invention as set forth in the appended claims.

I claim:

1. A method for determining the multi-phase fluid saturation in a porous media, comprising the steps of:
   (a) scanning a sample of said porous media with X-rays of differing energies,
   (b) producing computed tomographic images of said sample at said differing energies,
   (c) extracting the multi-phase fluid from said sample,
   (d) scanning said fluid-extracted sample with X-rays of said differing energies,
   (e) producing computed tomographic images of said fluid-extracted sample at said differing energies,
   (f) scanning said extracted fluids with X-rays at said differing energies,
   (g) producing computed tomographic images of said extracted fluids at said differing energies,
   (h) determining the X-ray mass attenuation coefficients for said sample and each of the fluid phases of said extracted fluids at each of said differing energies from said computed tomographic images,
   (i) determining the weight fractions of each of said fluid phases from said mass attenuation coefficients, and
   (j) determining the volume fractions of each of said fluid phases by multiplying said weight fractions by the densities of the respective fluid phases.

2. The method of claim 1 wherein said fluid-extracted sample is air-filled prior to being scanned with said X-rays.

3. The method of claim 2 wherein the extraction of the multi-phase fluid from said sample includes a first flushing with at least one solvent and a second flushing with air.

4. The method of claim 1 wherein scanning times in the order of one minute or greater are employed.

5. The method of claim 4 wherein said sample is cooled during X-ray scanning.

6. The method of claim 1 wherein the scanning of said extracted fluid with X-rays includes the separation of each phase of said fluid and the scanning of each phase independently.

7. The method of claim 1 wherein said differing energies are in the order of 100 and 150 kilovolts.

8. A method for determining three-phase fluid saturation in a porous media from the computed tomographic scanning of said media, comprising the steps of:

(a) scanning a sample of said porous media with X-rays of first and second energies, (b) producing computed tomographic numbers for said sample at said first and second energies, (c) extracting the three-phase fluid from said sample, (d) scanning the fluid extracted sample with X-rays of said first and second energies, (e) producing computed tomographic numbers for said fluid extracted sample at said first and second energies, (f) scanning said extracted fluid with X-rays at said first and second energies, (g) producing computed tomographic numbers for each phase of said extracted fluid at said first and second energies, (h) determining X-ray mass attenuation coefficients for said sample and each phase of said extracted fluid at each of said first and second energies from said computed tomographic numbers in accordance with the following expression:

$$N_{CT} = (\mu_M - \mu_W)/\mu_W \times 1000$$

where $N_{CT}$ = computed tomographic number,
$\mu$ = X-ray mass attenuation coefficient,
M = material scanned, and
W = water, (i) determining the weight fractions of each phase of said extracted fluid from said X-ray mass attenuation coefficients in accordance with the following expressions:

$$\mu_{M(1)} = X_a\mu_{a(1)} + X_b\mu_{b(1)} + X_c\mu_{c(1)},$$

$$\mu_{M(2)} = X_a\mu_{a(2)} + X_b\mu_{b(2)} + X_c\mu_{c(2)},$$

$$1 = X_a + X_b + X_c,$$

where $X_a$, $X_b$, and $X_c$ are the weight fractions for the three fluid phases a, b, and c; and (1) and (2) are the first and second energies; and (j) determining the volume fractions of each phase of said extracted fluid by multiplying said weight fractions by the densities of the respective fluid phases.

9. The method of claim 8 wherein the computed tomographic number utilized in step (h) for the determination of the mass attenuation coefficient for said sample is the difference of the computed tomographic numbers of the fluid saturated sample and fluid extracted sample determined in steps (b) and (e).

* * * * *